United States Patent [19]

Allen

[11] 4,273,772

[45] Jun. 16, 1981

[54] METHOD OF REDUCING GASTRIC SECRETION

[75] Inventor: Richard C. Allen, Flemington, N.J.

[73] Assignee: Hoechst-Roussel Pharmaceuticals, Inc., Bridgewater, N.J.

[21] Appl. No.: 67,223

[22] Filed: Aug. 17, 1979

[51] Int. Cl.³ .................. A61K 27/00; A61K 31/495; A61K 31/445; A61K 31/40

[52] U.S. Cl. ............................. 424/248.54; 424/248.4; 424/248.57; 424/250; 424/267; 424/273 R; 424/274

[58] Field of Search .............. 424/274, 248.54, 248.56, 424/248.57, 248.4, 267, 250, 273 R

[56] References Cited

U.S. PATENT DOCUMENTS

| | | | |
|---|---|---|---|
| 3,997,557 | 12/1976 | Helsley | 424/248.54 |
| 4,021,448 | 5/1977 | Bell | 424/274 |
| 4,069,337 | 1/1978 | Bell | 424/274 |

*Primary Examiner*—Frederick E. Waddell
*Attorney, Agent, or Firm*—Curtis, Morris & Safford

[57] ABSTRACT

This invention relates to a method of reducing gastric secretion or ulcer formation and more particularly, to reducing such secretion or formation in mammals with a substituted N-aminoalkylpyrrole.

32 Claims, No Drawings

METHOD OF REDUCING GASTRIC SECRETION

BACKGROUND OF THE INVENTION

1. Field of the Invention

This invention relates to a method of reducing gastric secretion or ulcer formation and more particularly, to reducing such secretion or formation in mammals, including humans, with a substituted N-aminoalkylpyrrole.

2. Discussion of the Prior Art

It is known in the art that 2-substituted-indole-lower alkanecarboxamides have anti-secretory or anti-ulcer activity, as reported in U.S. Pat. Nos. 4,021,448 and 4,069,337. U.S. Pat. No. 3,997,557 reveals substituted N-aminoalkylpyrroles, of the subject invention, which are disclosed as having antiarrhythmic, central nervous system depressant, antiinflammatory and antihypertensive activity. No literature has been found that discloses or suggests the use of such substituted N-aminoalkylpyrroles as anti-secretory or anti-ulcer agents.

SUMMARY OF THE INVENTION

This invention relates to a method of reducing gastric secretion or ulcer formation and more particularly, to reducing such secretion or formation in mammals with a substituted N-aminoalkylpyrrole.

The method comprises administering to a mammal an effective anti-secretory amount or an effective anti-ulcer amount of a substituted N-aminoalkylpyrrole having the formula

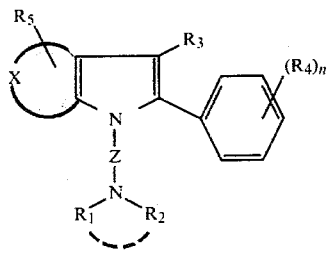

wherein Z is a straight or branched saturated or olefinically unsaturated hydrocarbon chain of from 2 to 5 carbon atoms; $R_1$ is hydrogen or alkyl of from 1 to 3 carbon atoms; $R_2$ is alkyl of from 1 to 3 carbon atoms or phenyl; or $R_1$ and $R_2$ together with the nitrogen atom to which they are attached form a heterocyclic selected from the group consisting of pyrrolidinyl, piperidino, piperazinyl, imidazolidonyl and morpholino; $R_3$ is hydrogen or phenyl or substituted phenyl; $R_4$ is alkyl of from 1 to 6 carbon atoms, alkoxy of from 1 to 4 carbon atoms, halogen, trifluoromethyl, hydroxy, nitro, cyano, amino, acetamido, phenyl or substituted phenyl; n is an integer from 0 to 3, inclusive; X is alkylene of from 3 to 7 carbon atoms; and $R_5$ is hydrogen, alkyl of from 1 to 5 carbon atoms, alkoxy of from 1 to 2 carbon atoms or halogen; or a physiological tolerable acid addition salt thereof.

DETAILED DESCRIPTION

This invention relates to a method of treatment with substituted N-aminoalkylpyrroles having useful anti-secretory and anti-ulcer activities and having the formula

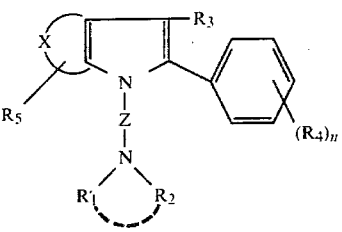

wherein Z represents a straight or branched, saturated or olefinically unsaturated hydrocarbon chain of 2–5 carbon atoms; $R_1$ represents a hydrogen atom or loweralkyl of from 1–3 carbon atoms; $R_2$ represents loweralkyl of from 1–3 carbon atoms or phenyl; or $R_1$ and $R_2$ together with the nitrogen atom to which they are attached form a heterocycle selected from the group consisting of pyrrolidinyl, piperidino, piperazinyl, imidazolidonyl and morpholino; $R_3$ represents a hydrogen atom, phenyl or substituted phenyl; $R_4$ can be situated meta, ortho or para and represents alkyl of from 1–6 carbon atoms, alkoxy of from 1–4 carbon atoms, halogen, trifluoromethyl, hydroxy, nitro, amino, cyano, acetamido, unsubstituted or substituted phenyl; n is the integer 0, 1, 2 or 3; and X is alkylene of from 3–7 carbon atoms,

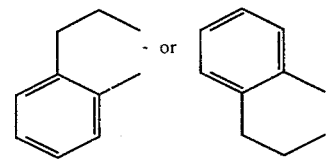

and $R_5$ is hydrogen, alkyl of from 1–5 carbon atoms, alkoxy of from 1–2 carbon atoms, or halogen; and their physiologically tolerable acid addition salts. The above compounds and their preparation are fully described in U.S. Pat. No. 3,997,557 which is incorporated by reference hereinto. Some typical compounds include:

1-(2-dimethylaminoethyl)-2-phenyl-4,5,6,7-tetrahydroindole;

1-[2-(1-imidazolidonylethyl)]-2-phenyl-4,5,6,7-tetrahydroindole;

1-(2-dimethylaminoethyl)-2-(p-methoxyphenyl)-4,5,6,7-tetrahydroindole;

1-(3-dimethylaminopropyl)-2-(p-methoxyphenyl)-4,5,6,7-tetrahydroindole;

2-(p-bromophenyl)-1-(3-dimethylaminopropyl)-4,5,6,7-tetrahydroindole;

2-(p-bromophenyl)-1-[2-(1-morpholinoethyl)]-4,5,6,7-tetrahydroindole;

1-(2-methylaminoethyl)-2-(m-trifluoroethylphenyl)-4,5,6,7-tetrahydroindole;

1-(3-dimethylaminopropyl)-2-(p-chlorophenyl)-4,5,6,7-tetrahydroindole;

1-(2-isopropylaminopropyl)-2-(p-chlorophenyl)-4,5,6,7-tetrahydroindole;

2-(p-hydroxyphenyl-1-(2-isopropylaminoethyl)-4,5,6,7-tetrahydroindole;

1-(2-diisopropylaminoethyl)-2-(p-hydroxyphenyl)-4,5,6,7-tetrahydroindole;

1-(2-diethylaminoethyl)-2-phenyl-5-methyl-4,5,6,7-tetrahydroindole;

1-(2-diethylaminoethyl)-2-phenyl-5-(t-butyl)-4,5,6,7-tetrahydroindole;
1-(2-diethylaminoethyl)-2-phenyl-5-methoxy-4,5,6,7-tetrahydroindole;
1-(2-isopropylaminoethyl)-2-(3,4-dichlorophenyl)-4,5,6,7-tetrahydroindole;
1-(3-dimethylaminopropyl)-2,3-diphenyl-4,5,6,7-tetrahydroindole;
1-[3-(1-pyrrolidinopropyl)]-2-(p-fluorophenyl)-4,5,6,7-tetrahydroindole;
1-(3-dimethylaminopropyl)-2-phenyl-4,5-dihydrobenz[g]indole;
1-(3-dimethylaminopropyl)-2-phenyl-4,5-dihydrobenz[e]indole;
1-(3-diethylaminopropyl)-4,5-dihydro-2-phenylbenz[e]indole;
1-(3-methylaminopropyl)-2-phenyl-7-chloro-4,5-dihydrobenz[e]indole;
1-(3-methylaminopropyl)-2-phenyl-1,4,5,6-tetrahydrocyclopenta[b]pyrrole;
1-(2-methylaminoethyl)-2-(m-trifluoromethylphenyl)-1,4,5,6,7,8-hexahydrocyclohepta[b]pyrrole;
1-(3-dimethylaminopropyl)-2-(p-methoxyphenyl)-1,4,5,6,7,8-hexahydrocyclohepta[be]pyrrole;
1-(3-methylaminopropyl)-2-(p-methoxyphenyl)-1,4,5,6,7,8-hexahydrocyclohepta[be]pyrrole;
1-(3-dimethylaminopropyl)-2-(p-bromophenyl)-1,4,5,6,7,8-hexahydrocyclohepta[b]pyrrole;
1-(3-dimethylaminopropyl)-2-(p-cyanophenyl)-1,4,5,6,7,8-hexahydrocyclohepta[b]pyrrole;
1-(3-dimethylaminopropyl)-2-(p-nitrophenyl)-1,4,5,6,7,8-hexahydrocyclohepta[b]pyrrole;
1-(3-dimethylaminopropyl)-2-(p-aminophenyl)-1,4,5,6,7,8-hexahydrocyclohepta[b]pyrrole;
1-(3-dimethylaminopropyl)-2-(3,4,5-trimethoxyphenyl)-1,4,5,6,7,8-hexahydrocyclohepta[b]pyrrole;
1-(3-dimethylaminopropyl)-2-(p-fluorophenyl)-1,4,5,6,7,8-hexahydrocyclohepta[b]pyrrole;
1-(3-dimethylaminopropyl)-2-phenyl-4,5,6,7,8,9-hexahydrocycloocta[b]pyrrole;
1-(2-ethylaminoethyl)-2-phenyl-4,5,6,7,8,9-hexahydrocycloocta[b]pyrrole;
1-(3-dimethylaminopropyl)-2-(p-nitrophenyl)-4,5,6,7,8,9-hexahydrocycloocta[b]pyrrole;
1-(3-dimethylaminopropyl)-2-(p-aminophenyl)-4,5,6,7,8,9-hexahydrocycloocta[b]pyrrole;
1-(3-dimethylaminopropyl)-2-(p-fluorophenyl)-4,5,6,7,8,9-hexahydrocycloocta[b]pyrrole;
1-(3-dimethylaminopropyl)-2-(p-methoxyphenyl)-4,5,6,7,8,9-hexahydroocta[b]pyrrole;
1-(3-methylaminopropyl)-2-phenyl-4,5,6,7-tetrahydrodinole;
2-(p-bromophenyl)-1-(3-dimethylaminopropyl)-1,4,5,6,7,8-hexahydrocyclohepta[b]pyrrole;
2-(p-cyanophenyl)-1-(3-dimethylaminopropyl)-1,4,5,6,7,8-hexahydrocyclohepta[b]pyrrole;
1-(3-methylaminopropyl)-2-phenyl-7-chloro-4,5-dihydrobenz-[e]indole;
1-(3-diethylaminopropyl)-2-(p-methoxyphenyl)-4,5,6,7,8,9-hexahydrocycloocta[b]pyrrole;
1-(4-diethylamino-2-butenyl)-2-phenyl-4,5,6,7-tetrahydroindole hydrochloride;
1-(3-dimethylaminopropyl)-2-phenyl-1,4,5,6-tetrahydrocyclopenta[b]pyrrole;
1-(2-methylaminoethyl)-2-phenyl-1,4,5,6,7,8-hexahydrocyclohepta[b]pyrrole;
1-(3-diethylaminopropyl)-2-phenyl-1,4,5,6,7,8-hexahydrocyclohepta[b]pyrrole;
1-(3-diethylaminopropyl)-2-phenyl-1,4,5,6,7,8-hexahydrocyclohepta[b]pyrrole; and
1-(1-methyl-2-dimethylaminoethyl)-2-phenyl-1,4,5,6,7,8-hexahydrocyclohepta[b]pyrrole; and the physiologically acceptable salts of the above compounds.

These compounds are prepared as described in U.S. Pat. No. 3,997,557. Most advantageously, the compounds of the present invention are prepared by condensation of an appropriate γ-diketone with an appropriate aminoalkylamine or aminoalkyleneamine as illustrated in the following equation:

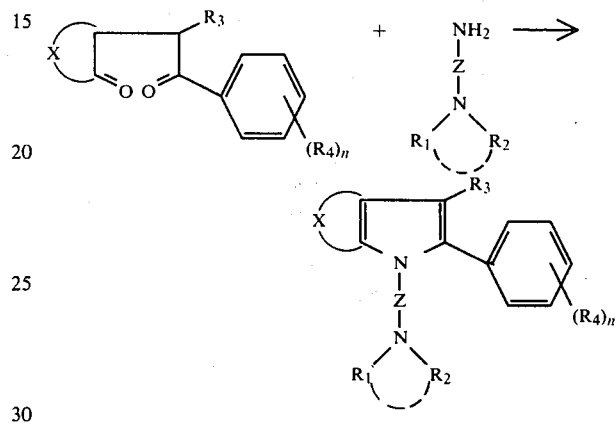

wherein X, Z, n, $R_1$, $R_2$ and $R_4$ are as defined earlier. In one procedure, the γ-diketone and the aminoalkylamine are allowed to react, with or without a solvent such as acetic acid or ethanol, at a temperature between 50°–120° C., for a period of time from several minutes to 24 hours in the presence or absence of an acidic catalyst such as hydrochloric acid.

When $R_4$ represents $NO_2$, the nitro can be reduced by methods known to the art such as by shaking a solution of the corresponding compound of the invention in glacial acetic acid on the Parr Hydrogenator with a Pd on carbon catalyst. Also, when $R_4$ represents Br, the bromo can be displaced with a cyano group by methods known to the art such as by reacting with cuprous cyanide.

The anti-secretory activity and the anti-ulcer activity of the substituted N-alkylaminopyrroles of this invention can be demonstrated using conventional, standard biological test procedures, such as those described in U.S. Pat. No. 4,021,448 and 4,069,337. In particular, the procedure of Shay et al. Gastroenterology 5, 43 (1945) may be employed to determine anti-secretory activity. The anti-ulcer activity of the substituted N-alkylaminopyrroles can be determined using the method described by Selmici et al. Acta. Physiol. Acad. Sci. Hung. 25(1), 101–104 (1964).

It is of course understood that the actual determination of the biological data definitive for any particular compound of the invention is readily determined by standard test procedures by technicians versed in pharmacological test procedures without an undue amount of experimentation.

The substituted N-alkylaminopyrroles are administered in an effective amount sufficient to inhibit in mammals, secretion of gastric fluids and/or to inhibit stomach ulceration, typically in an amount of from 10 mg/kg of body weight per day to 200 mg/kg of body weight per day. The compounds are preferably administered orally.

The substituted N-alkylaminopyrrole compounds can be prepared for use by incorporation in unit dosage form as tablets or capsules for oral administration to patients or animals either alone or in combination with suitable adjuvants such as calcium carbonate, starch, lactose, sodium bicarbonate, sodum lauryl sulfate, sugar, dextrose, mannitol, cellulose, gum acacia and the like. Alternatively, they can be formulated for oral administration in aqueous alcohol, glycol or oil solutions or oil-water emulsions in the same manner as conventional medicinal substances are prepared. They can also be formulated for oral use with foodstuffs or admixed with foodstuffs for veterinary use.

I claim:

1. A method of reducing gastric secretion in a mammal which comprises administering to a mammal in need thereof an effective anti-secretory amount of a substituted N-aminoalkylpyrrole having the formula

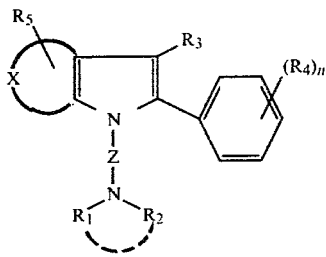

wherein Z is a straight or branched saturated or olefinically unsaturated hydrocarbon chain of from 2 to 5 carbon atoms; $R_1$ is hydrogen or alkyl of from 1 to 3 carbon atoms; $R_2$ is alkyl of from 1 to 3 carbon atoms or phenyl; or $R_1$ and $R_2$ together with the nitrogen atom to which they are attached form a heterocyclic selected from the group consisting of pyrrolidinyl, piperidino, piperazinyl, imidazolidonyl and morpholino; $R_3$ is hydrogen or phenyl or substituted phenyl; $R_4$ is alkyl of from 1 to 6 carbon atoms; alkoxy of from 1 to 4 carbon atoms; halogen, trifluoromethyl, hydroxy, nitro, cyano, amino, acetamido, phenyl or substituted phenyl; n is an integer from 0 to 3, inclusive; X is alkylene of from 3 to 7 carbon atoms; and $R_5$ is hydrogen, alkyl of from 1 to 5 carbon atoms, alkoxy of from 1 to 2 carbon atoms or halogen; or a physiological tolerable acid addition salt thereof.

2. A method as defined in claim 1 wherein Z is a straight or branched, saturated hydrocarbon chain of from 2 to 3 carbon atoms; $R_3$ is hydrogen or phenyl; $R_4$ is methyl, methoxy, bromo, chloro, fluoro, hydroxy, trifluoromethyl, nitro, amino or cyano; X is polymethylene of from 3 to 6 carbon atoms; and $R_5$ is hydrogen, alkyl of from 1 to 4 carbon atoms or methoxy.

3. The method as defined in claim 2 wherein said substituted N-aminoalkyl pyrrole is 1-(3-dimethylaminopropyl)-2-phenyl-1,4,5,6-tetrahydrocyclopenta[b]pyrrole and the physiologically tolerable acid addition salts thereof.

4. The method as defined in claim 2 wherein said substituted N-aminoalkyl pyrrole is 1-(3-dimethylaminopropyl)-2-(p-bromophenyl)-4,5,6,7-tetrahydroindole and the physiologically tolerable acid addition salts thereof.

5. The method as defined in claim 2 wherein said substituted N-aminoalkyl pyrrole is 1-(3-dimethylaminopropyl)-2-(p-methoxyphenyl)-4,5,6,7-tetrahydroindole and the physiologically tolerable acid addition salts thereof.

6. The method as defined in claim 2 wherein said substituted N-aminoalkyl pyrrole is 1-(2-methylaminoethyl)-2-(m-trifluoromethylphenyl)-4,5,6,7-tetrahydroindole and the physiologically tolerable acid addition salts thereof.

7. The method as defined in claim 2 wherein said substituted N-aminoalkyl pyrrole is 1-(3-dimethylaminopropyl)-2,3-diphenyl-4,5,6,7-tetrahydroindole and the physiologically tolerable acid addition salts thereof.

8. The method defined in claim 2 wherein said substituted N-aminoalkyl pyrrole is 1-(2-methylaminoethyl)-2-phenyl-1,4,5,6,7,8-hexahydrocyclohepta[b]pyrrole and the physiologically tolerable acid addition salts thereof.

9. The method defined in claim 2 wherein said substituted N-aminoalkyl pyrrole is 1-(3-diethylaminopropyl)-2-phenyl-1,4,5,6,7,8-hexahydrocyclohepta[b]pyrrole and the physiologically tolerable acid addition salts thereof.

10. The method as defined in claim 2 wherein said substituted N-aminoalkyl pyrrole is 1-(3-diethylaminopropyl)-2-phenyl-1,4,5,6,7,8-hexahydrocyclohepta[b]pyrrole and the physiologically tolerable acid addition salts thereof.

11. The method as defined in claim 2 wherein said substituted N-aminoalkyl pyrrole is 1-(1-methyl-2-dimethylaminoethyl)-2-phenyl-1,4,5,6,7,8-hexahydrocyclohepta[b]pyrrole and the physiologically tolerable acid addition salts thereof.

12. The method as defined in claim 2 wherein said substituted N-aminoalkyl pyrrole is 1-(3-methylaminopropyl)-2-(p-methoxyphenyl)-1,4,5,6,7,8-hexahydrocyclohepta[b]pyrrole and the physiologically tolerable acid addition salts thereof.

13. The method as defined in claim 2 wherein said substituted N-aminoalkyl pyrrole is 1-(2-ethylaminoethyl)-2-phenyl-4,5,6,7,8,9-hexahydrocycloocta[b]pyrrole and the physiologically tolerable acid addition salts thereof.

14. The method as defined in claim 2 wherein said substituted N-aminoalkyl pyrrole is 1-(3-dimethylaminopropyl)-2-(p-aminophenyl)-4,5,6,7,8,9-hexahydrocycloocta[b]pyrrole and the physiologically tolerable acid addition salts thereof.

15. A method of reducing incidence of ulcer formation in a mammal which comprises administering to a mammal in need thereof an effective anti-ulcer amount of a substituted N-aminoalkylpyrrole having the formula

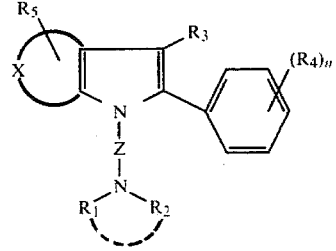

wherein Z is a straight or branched saturated or olefinically unsaturated hydrocarbon chain of from 2 to 5 carbon atoms; $R_1$ is hydrogen or alkyl of from 1 to 3 carbon atoms; $R_2$ is alkyl of from 1 to 3 carbon atoms or phenyl; or $R_1$ and $R_2$ together with the nitrogen atom to which they are attached form a heterocyclic selected from the group consisting of pyrrolidinyl, piperidino, piperazinyl, imidazolidonyl and morpholino; $R_3$ is hydrogen or phenyl or substituted phenyl; $R_4$ is alkyl of from 1 to 6 carbon atoms; alkoxy of from 1 to 4 carbon atoms, halogen, trifluoromethyl, hydroxy, nitro, cyano, amino, acetamido, phenyl or substituted phenyl; n is an integer from 0 to 3, inclusive; X is alkylene of from 3 to 7 carbon atoms; and $R_5$ is hydrogen, alkyl of from 1 to 5 carbon atoms, alkoxy of from 1 to 2 carbon atoms or halogen; or a physiological tolerable acid addition salt thereof.

16. A method as defined in claim 15 wherein Z is a straight or branched, saturated hydrocarbon chain of from 2 to 3 carbon atoms; $R_3$ is hydrogen or phenyl; $R_4$ is methyl, methoxy, bromo, chloro, fluoro, hydroxy, trifluoromethyl, nitro, amino or cyano; X is polymethylene of from 3 to 6 carbon atoms; and $R_5$ is hydrogen, alkyl of from 1 to 4 carbon atoms or methoxy.

17. The method as defined in claim 15 wherein said substituted N-aminoalkyl pyrrole is 1-(3-dimethylaminopropyl)-2-phenyl-1,4,5,6-tetrahydrocyclopenta[b]pyrrole and the physiologically tolerable acid addition salts thereof.

18. The method as defined in claim 15 wherein said substituted N-aminoalkyl pyrrole is 1-(3-dimethylaminopropyl)-2-(p-bromophenyl)-4,5,6,7-tetrahydroindole and the physiologically tolerable acid addition salts thereof.

19. The method as defined in claim 15 wherein said substituted N-aminoalkyl pyrrole is 1-(3-dimethylaminopropyl)-2-(p-methoxyphenyl)-4,5,6,7-tetrahydroindole and the physiologically tolerable acid addition salts thereof.

20. The method as defined in claim 15 wherein said substituted N-aminoalkyl pyrrole is 1-(2-methylaminoethyl)-2-(m-trifluoromethylphenyl)-4,5,6,7-tetrahydroindole and the physiologically tolerable acid addition salts thereof.

21. The method as defined in claim 15 wherein said substituted N-aminoalkyl pyrrole is 1-(3-dimethylaminopropyl)-2,3-diphenyl-4,5,6,7-tetrahydroindole and the physiologically tolerable acid addition salts thereof.

22. The method as defined in claim 15 wherein said substituted N-aminoalkyl pyrrole is 1-(2-methylaminoethyl)-2-phenyl-1,4,5,6,7,8-hexahydrocyclohepta[b]pyrrole and the physiologically tolerable acid addition salts thereof.

23. The method as defined in claim 15 wherein said substituted N-aminoalkyl pyrrole is 1-(3-diethylaminopropyl)-2-phenyl-1,4,5,6,7,8-hexahydrocyclohepta[b]pyrrole and the physiologically tolerable acid addition salts thereof.

24. The method as defined in claim 15 wherein said substituted N-aminoalkyl pyrrole is 1-(3-diethylaminopropyl)-2-phenyl-1,4,5,6,7,8-hexahydrocyclohepta[b]pyrrole and the physiologically tolerable acid addition salts thereof.

25. The method as defined in claim 15 wherein said substituted N-aminoalkyl pyrrole is 1-(1-methyl-2-dimethylaminoethyl)-2-phenyl-1,4,5,6,7,8-hexahydrocyclohepta[b]pyrrole and the physiologically tolerable acid addition salts thereof.

26. The method as defined in claim 15 wherein said substituted N-aminoalkyl pyrrole is 1-(3-methylaminopropyl)-2-(p-methoxyphenyl)-1,4,5,6,7,8-hexahydrocyclohepta[b]pyrrole and the physiologically tolerable acid addition salts thereof.

27. The method as defined in claim 15 wherein said substituted N-aminoalkyl pyrrole is 1-(2-ethylaminoethyl)-2-phenyl-4,5,6,7,8,9-hexahydrocycloocta[b]pyrrole and the physiologically tolerable acid addition salts thereof.

28. The method as defined in claim 15 wherein said substituted N-aminoalkyl pyrrole is 1-(3-dimethylaminopropyl)-2-(p-aminophenyl)-4,5,6,7,8,9-hexahydrocycloocta[b]pyrrole and the physiologically tolerable acid addition salts thereof.

29. A method of reducing gastric secretion in a mammal which comprises administering to a mammal in need thereof an effective anti-secretory amount of a substituted N-aminoalkylpyrrole having the formula

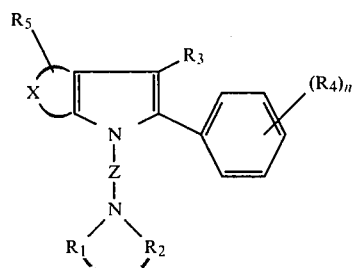

wherein Z is a straight or branched saturated or olefinically unsaturated hydrocarbon chain of from 2 to 5 carbon atoms; $R_1$ is hydrogen or alkyl of from 1 to 3 carbon atoms; $R_2$ is alkyl of from 1 to 3 carbon atoms or phenyl; $R_3$ is hydrogen or phenyl or substituted phenyl; $R_4$ is alkyl of from 1 to 6 carbon atoms, alkoxy of from 1 to 4 carbon atoms, halogen, trifluoromethyl, hydroxy, nitro, cyano, amino, acetamido, phenyl or substituted phenyl; n is an integer from 0 to 3, inclusive; X is alkylene of from 3 to 7 carbon atoms; and $R_5$ is hydrogen, alkyl of from 1 to 5 carbon atoms, alkoxy of from 1 to 2 carbon atoms or halogen; or a physiological tolerable acid addition salt thereof.

30. A method of reducing gastric secretion in a mammal which comprises administering to a mammal in need thereof an effective anti-secretory amount of a substituted N-aminoalkylpyrrole of the formula

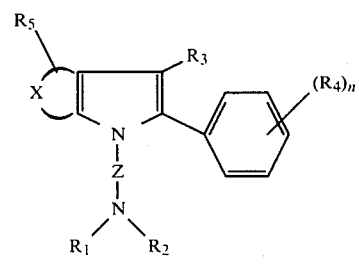

wherein Z is a straight or branched saturated or olefinically unsaturated hydrocarbon chain of from 2 to 5 carbon atoms; $R_1$ and $R_2$ together with the nitrogen atom to which they are attached form a heterocyclic selected from the group consisting of pyrrolidinyl, piperidino, piperazinyl, imidazolidonyl and morpholino; $R_3$ is hydrogen or phenyl or substituted phenyl; $R_4$ is alkyl of from 1 to 6 carbon atoms, alkoxy of from 1 to 4 carbon atoms, halogen, trifluoromethyl, hydroxy, nitro, cyano, amino, acetamido, phenyl or substituted phenyl; n is an integer from 0 to 3, inclusive; X is alkylene of from 3 to 7 carbon atoms; and $R_5$ is hydrogen, alkyl of from 1 to 5 carbon atoms, alkoxy of from 1 to 2 carbon atoms or halogen; or a physiological tolerable acid addition salt thereof.

31. A method of reducing incidence of ulcer formation in a mammal which comprises administering to a mammal in need thereof an effective anti-ulcer amount of a substituted N-aminoalkylpyrrole having the formula

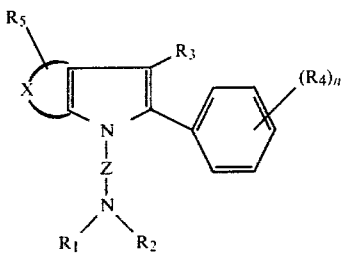

wherein Z is a straight or branched saturated or olefinically unsaturated hydrocarbon chain of from 2 to 5 carbon atoms; $R_1$ is hydrogen or alkyl of from 1 to 3 carbon atoms; $R_2$ is alkyl of from 1 to 3 carbon atoms or phenyl; $R_3$ is hydrogen or phenyl or substituted phenyl; $R_4$ is alkyl of from 1 to 6 carbon atoms, alkoxy of from 1 to 4 carbon atoms, halogen, trifluoromethyl, hydroxy, nitro, cyano, amino, acetamido, phenyl or substituted phenyl; n is an integer from 0 to 3, inclusive; X is alkylene of from 3 to 7 carbon atoms; and $R_5$ is hydrogen, alkyl of from 1 to 5 carbon atoms, alkoxy of from 1 to 2 carbon atoms or halogen; or a physiological tolerable acid addition salt thereof.

32. A method of reducing incidence of ulcer formation in a mammal which comprises administering to a mammal in need thereof an effective anti-ulcer amount of a substituted N-aminoalkylpyrrole of the formula

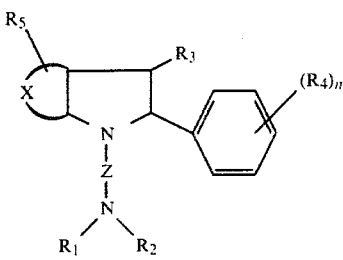

wherein Z is a straight or branched saturated or olefinically unsaturated hydrocarbon chain of from 2 to 5 carbon atoms; $R_1$ and $R_2$ together with the nitrogen atom to which they are attached form a heterocyclic selected from the group consisting of pyrrolidinyl, piperidino, piperazinyl, imidazolidonyl and morpholino; $R_3$ is hydrogen or phenyl or substituted phenyl; $R_4$ is alkyl of from 1 to 6 carbon atoms; alkoxy of from 1 to 4 carbon atoms, halogen, trifluoromethyl, hydroxy, nitro, cyano, amino, acetamido, phenyl or substituted phenyl; n is an integer from 0 to 3, inclusive; X is alkylene of from 3 to 7 carbon atoms; and $R_5$ is hydrogen, alkyl of from 1 to 5 carbon atoms, alkoxy of from 1 to 2 carbon atoms or halogen; or a physiological tolerable acid addition salt thereof.

* * * * *

UNITED STATES PATENT OFFICE
CERTIFICATE OF CORRECTION

Patent No. 4,273,772     Dated June 16, 1981

Inventor(s) Richard C. Allen

It is certified that error appears in the above-identified patent and that said Letters Patent are hereby corrected as shown below:

Column 3, lines 11-12 - change "...dihydrobenz[g]indole" to -- ...dihydrobenz[e]indole --

Column 3, lines 24 and 26 - change "...cyclohepta[be]pyrrole" to --...cyclohepta[b,e]pyrrole --

Signed and Sealed this

Fifteenth Day of September 1981

[SEAL]

Attest:

Attesting Officer

GERALD J. MOSSINGHOFF

Commissioner of Patents and Trademarks